(12) United States Patent
Kelley

(10) Patent No.: US 9,603,720 B2
(45) Date of Patent: Mar. 28, 2017

(54) OSTEOTOME GUIDE CONFIGURED TO ATTACH TO AN IMPLANTED FEMORAL COMPONENT

(71) Applicant: Scott Kelley, Chapel Hill, NC (US)

(72) Inventor: Scott Kelley, Chapel Hill, NC (US)

( * ) Notice: Subject to any disclaimer, the term of this patent is extended or adjusted under 35 U.S.C. 154(b) by 314 days.

(21) Appl. No.: 14/464,348

(22) Filed: Aug. 20, 2014

(65) Prior Publication Data

US 2015/0057666 A1 Feb. 26, 2015

Related U.S. Application Data

(60) Provisional application No. 61/869,935, filed on Aug. 26, 2013.

(51) Int. Cl.
*A61F 2/46* (2006.01)
*A61B 17/15* (2006.01)
(Continued)

(52) U.S. Cl.
CPC ............ *A61F 2/4607* (2013.01); *A61B 17/15* (2013.01); *A61B 17/154* (2013.01); *A61B 17/155* (2013.01); *A61B 17/17* (2013.01); *A61B 17/175* (2013.01); *A61B 17/1735* (2013.01); *A61B 17/1739* (2013.01); *A61B 17/1742* (2013.01); *A61F 2/46* (2013.01); *A61F 2/4603* (2013.01); *A61B 17/1604* (2013.01); *A61B 17/1668* (2013.01); *A61F 2002/30433* (2013.01); *A61F 2002/4619* (2013.01); *A61F 2002/4687* (2013.01)

(58) Field of Classification Search
CPC ..... A61B 17/15; A61B 17/154; A61B 17/155; A61B 17/17; A61B 17/1735; A61B 17/1739; A61B 17/1742; A61B 17/175; A61F 2/46; A61F 2/4603; A61F 2/4607; A61F 2002/4619

See application file for complete search history.

(56) References Cited

U.S. PATENT DOCUMENTS 5,257,995 A * 11/1993 Umber ............... A61B 17/8872
606/86 R
6,187,012 B1 * 2/2001 Masini ................... A61B 17/15
606/99

(Continued)

OTHER PUBLICATIONS

Callaghan et al., ed. The Adult Hip. vol. 2, 2nd ed. Chapter 60, pp. 884-910, and Chapter 70, pp. 1025-1035. 2007. Lippincott Williams & Wilkins, Philadephia, PA.

(Continued)

*Primary Examiner* — Larry E Waggle, Jr.
(74) *Attorney, Agent, or Firm* — Coats & Bennett, P.L.L.C.

(57) ABSTRACT

Guides configured to guide one or more osteotomes to remove a femoral component that is implanted in a femur. When implanted, the femoral component includes a stem implanted within the femur, a proximal end that extends from the femur, and a receptacle in the proximal end. The guides are configured to attach to the femoral component and attach to the receptacle in the femoral component. The guides include one or more openings sized to guide the osteotomes along the stem of the femoral component. The guides may further include multiple different sections that can be attached together.

20 Claims, 12 Drawing Sheets

(51) Int. Cl.
  *A61B 17/17* (2006.01)
  *A61B 17/16* (2006.01)
  *A61F 2/30* (2006.01)

(56) References Cited

U.S. PATENT DOCUMENTS

| | | | |
|---|---|---|---|
| 7,004,972 | B2 | 2/2006 | Yoon |
| 7,935,118 | B2 * | 5/2011 | Vendrely ............... A61B 17/17 606/87 |
| 2004/0236341 | A1 | 11/2004 | Petersen |
| 2011/0046745 | A1 | 2/2011 | Daniels et al. |
| 2011/0112540 | A1 | 5/2011 | McLean et al. |

OTHER PUBLICATIONS

Hansen et al. "The Rottinger approach for total hip arthroplasty: technique and review of the literature" Curr Rev. Musculoskelet Med (2011) 4:132-138. Springer, Berlin, Germany.
"Zimmer Natural-Hip™ System Surgical Technique" Informational Booklet. 25 pages. 2005. Zimmer, Inc. Warsaw, IN.
"CPT® 12/14 Hip System. Surgical Technique for Primary Hip Arthroplasty" Informational Booklet. 27 pages. 2002. Zimmer, Inc. Warsaw, IN.
"Alloclassic® Hip System Surgical Technique" Informational Booklet. 20 pages. 2003. Zimmer, Inc. Warsaw, IN.
"ZMR® Hip System" Informational literature, 20 pages. 2003. Zimmer, Inc. Warsaw, IN.
"Zimmer® M/L Taper Hip Prosthesis. Surgical Technique" Informational Booklet. 16 pages. 2010. Zimmer, Inc. Warsaw, IN.
"SYNERGY Cemented Stem Surgical Technique" Informational Booklet, 31 pages. 2004. Smith & Nephew, Inc., Memphis, TN.
"SYNERGY Cementless Stem Surgical Technique" Informational Booklet, 32 pages. 2004. Smith & Nephew, Inc., Memphis, TN.
"ZMR Revision Taper Hip Prosthesis, Surgical Technique for Revision Hip Arthroplasty" 26 pages. 1999. Zimmer, Inc. Warsaw, IN.
"Summit® titanium tapered stem." Product description and illustration,1 page. 2001. DePuy Orthopaedics, Inc., Warsaw, IN.
Morrey, Bernard, ed. Joint Replacement Arthroplasty. Chapter 44, pp. 619-638. 1991. Churchill Livingstone, Inc., New York, NY.
"DePuy Revision Solutions. Hip Extraction Instrumentation Product Overview." 16 pages. 2009. DePuy Orthopaedics, Inc. Warsaw, IN.
"Moreland Cementless Hip Revision Instrumentation." Product Overview. 12 pages. 1998. DePuy Orthopaedics, Inc. Warsaw, IN.

* cited by examiner

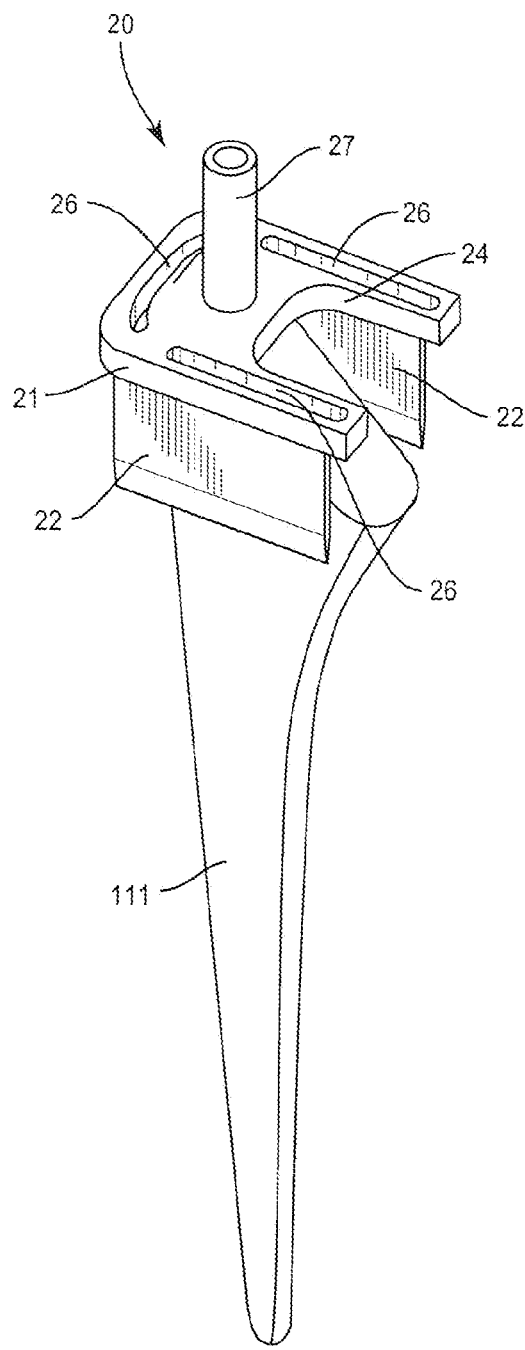
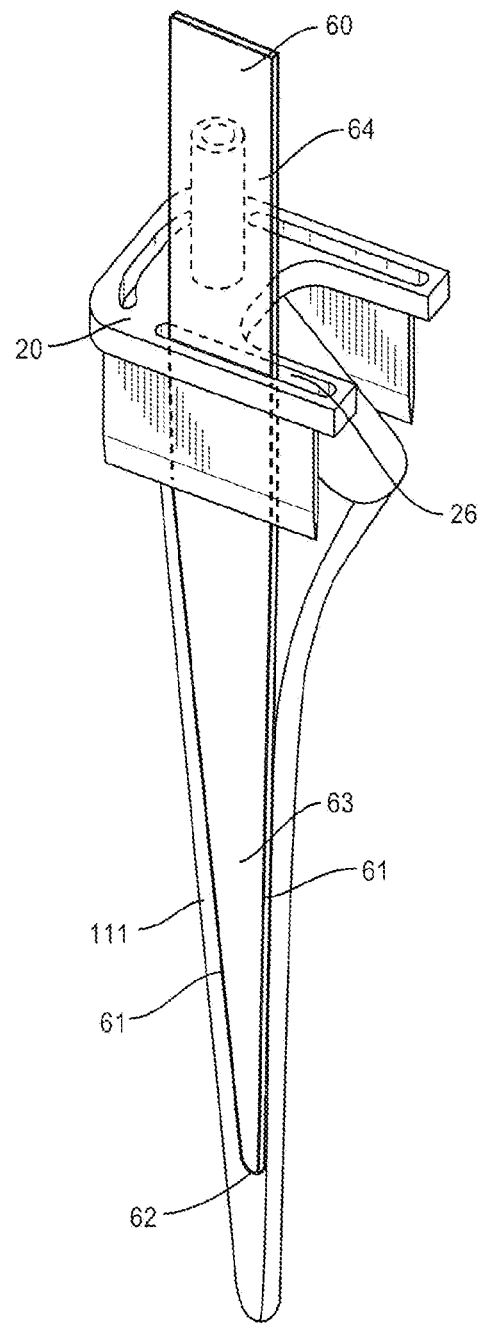
FIG. 5
FIG. 6

OSTEOTOME GUIDE CONFIGURED TO ATTACH TO AN IMPLANTED FEMORAL COMPONENT

CROSS-REFERENCE TO RELATED APPLICATIONS

The present application claims the benefit of U.S. Application No. 61/869,935 filed on Aug. 26, 2013, and entitled Osteotome Guide Configured to Attach to an Implanted Femoral Component. This application is hereby incorporated by reference in its entirety.

BACKGROUND

The present application is directed to an osteotome cutting guide that attaches to a femoral component that is implanted in a patient.

Hip replacement procedures involve the replacement of the hip joint formed by the head of the femur and the acetabulum of the pelvis. Hip replacement procedures include the preparation of the femur for receipt of a femoral component and preparation of the acetabulum to receive an acetabulum component. The two components engage together to replace the hip joint.

FIG. 1 illustrates a hip replacement implant 110 positioned within a patient. The implant 110 includes the femoral component 111 that is attached to the femur 100, and an acetabular component 113 that is attached to the acetabulum 101. The femoral component 111 includes a head 112 that seats within a receptacle of the acetabular component 113. This replacement joint replicates the hip joint and provides for pivoting movement of the femur 100 relative to the pelvis.

FIG. 2 illustrates one embodiment of a femoral component 111 mounted in a femur 100. The femoral component 111 includes an elongated shape that includes a stem 115, a neck 116, and a mount 117. The mount 117 is shaped to be inserted into a receptacle in the head 112. The head 112 includes a spherical exterior shape that engages with the acetabular component 113 in the pelvis 120.

A receptacle 118 is positioned at the neck 116 to receive an insertion rod (not illustrated) during insertion of the femoral component 111 into the femur 100. The receptacle 118 may be formed as a cavity that extends into the interior of the neck 116 and/or stem 115. The receptacle 118 may include threads or other engagement mechanisms that are configured to receive the insertion rod. During the implantation process, the insertion rod is mounted to the receptacle 118 to facilitate insertion and placement of the femoral component 111 within the femur 100. Once the femoral component 111 is implanted, the insertion rod is disengaged from the receptacle 118 and removed from the patient.

FIG. 2 illustrates a femoral component 111 implanted within the femur 100 and an acetabular component 113 mounted to the pelvis 120. For the femoral component 111, the neck 116, mount 117, and head 112 extend outward beyond the proximal end of the femur 100. At least a portion of the receptacle 118 is also exposed beyond the femur 110.

In some instances, it is necessary to remove the femoral component 111 from the femur 100 at a subsequent point in time after the implantation procedure. An infection is one instance in which removal is necessary. Various methods are used to remove the femoral component 111 from the femur 100. One method includes splitting the femur 100 to remove the femoral component 111. This method is usually performed when other options are not available. A more desirable method includes the use of flexible osteotomes that are inserted along the femoral component 111. The osteotomes cut the bone surrounding the femoral component 111 to allow for removal from the femur 100.

A problem with this procedure is inserting the osteotomes between the femoral component 111 and the femur 100 without damaging or splitting the femur 100. The osteotomes should be inserted against or in close proximity to the femoral component 111 to eliminate or reduce unnecessary cutting of the bone. However, this is often difficult for the surgeon. A relatively rigid osteotome is difficult to maintain against the femoral component 111. A relatively thin osteotome is easier to maintain against the femoral component 111. However, thinner osteotomes may bend and move away from the femoral component during cutting.

SUMMARY

The patent application is directed to devices and methods for guiding cutting tools for removing a femoral component from a femur. The devices attached to a proximal end of a femoral component that is implanted within a femur.

One embodiment is directed to a guide configured to direct one or more osteotomes to remove a femoral component that is implanted in a femur. The guide includes a body with a closed end and opposing sides that are spaced apart and extend from the closed end. The body includes an open end formed between the sides and opposite from the closed end. The body forms an interior space between the sides and the closed end with the open end leading into the interior space. The body is sized to extend partially around a perimeter of the femoral component when the femoral component is positioned in the interior space. The body includes a thickness measured between an inner side wall that faces into the interior space and an opposing outer side wall. An extension extends outward from one of the closed end and the sides and over the interior space. The extension is sized to extend over the proximal end of the femoral component. A connector is positioned in and extends from the extender to mount in the receptacle to attach the guide to the femoral component.

The guide may also include a flange that extends outward from a bottom side of the body and includes a sharpened tip to cut into the femur. The flange may extend outward from each of the closed end and the opposing sides.

The guide may include a slot that is enclosed within and that extends through the body. The slot may include an inlet at a top side of the body and an outlet at the bottom side of the body with the slot extending through the body between the flange and the inner side wall.

Openings may extend through the body from the top side to the bottom side with the openings being smaller than the slot may also extend through the body between the flange and the inner side wall.

The flange may include a smaller thickness than the body.

The guide may also include an attachment body configured to removably attach to the sides of the body and extend across the open end to fully enclose the interior space. The attachment body and the sides may include attachment mechanisms that engage together to removably attach the attachment body to the sides.

The guide may also include a tube that is attached to and extends from the extension with the tube including an opening sized to receive the connector.

Another embodiment is directed to a guide configured to guide one or more osteotomes to remove a femoral component that is implanted in a femur. The guide includes a U-shaped body with a closed end and opposing sides with inner side walls that form an interior space with an open end sized to receive the femoral component. The body includes a top side that faces away from the femur when positioned on the femoral component and an opposing bottom side. One or more elongated slots are enclosed within and that extend through the body from the top side to the bottom side. The one or more slots are sized to receive the osteotomes with each including an inlet at the top side and an outlet at the bottom side of the body. A flange extends from the bottom side of the body and includes a sharpened tip to cut into the femur. The flange positioned between the one or more elongated slots and outer side walls of the body.

The flange may be divided into two or more separate sections that each extend around different sections of the body.

The flange may have a thickness measured between an inner side and an outer side with the thickness of the flange being smaller than the body.

The guide may also include an attachment body removably attached to the body to enclose the interior space with each of the body and the attachment body including attachment members that engage together to removably attach the attachment body to the body.

The guide may include an extension that extends from the top side of the body over the interior space and over the receptacle in the femoral component when the body is positioned around the femoral component. The extension may be spaced away from the open end.

The may include a connector that extends outward from the extension to engage with the receptacle in the femoral component to attach the guide to the femoral component.

Another embodiment is directed to a guide configured to guide one or more osteotomes to remove a femoral component that is implanted in a femur. The guide includes a body with a closed end and opposing sides that are spaced apart and extend from the closed end. The body includes an open end formed between the sides and opposite from the closed end. The body forms an interior space between the sides and the closed end with the open end leading into the interior space. The body is sized to extend partially around a perimeter of the femoral component when the femoral component is positioned in the interior space. The body includes a top side that faces away from the femur when positioned on the femoral component and an opposing bottom side. An extension extends outward from the top side of the body and over the interior space. The extension is sized to extend over the proximal end of the femoral component when the femoral component is positioned in the interior space. A connector is positioned in and extends from the extension to mount in the receptacle to attach the guide to the femoral component. One or more elongated slots extend through the body from the top side to the bottom side. The one or more slots are each sized to receive the osteotomes and each includes an inlet at the top side and an outlet at the bottom side of the body. A flange extends from the bottom side of the body and includes a sharpened tip to cut into the femur. The flange extends from the bottom side of the body between the one or more elongated slots and the inner sidewalls.

The guide may also include a tube that extends from the extension and is sized to receive the connector.

The flange is divided into two or more separate sections that each extend around different sections of the body.

The flange comprises a thickness measured between an inner side and an outer side with the thickness of the flange being smaller than the body.

The guide may also include an attachment body removably attached to the body to enclose the interior space. Each of the body and the attachment body may include attachment members that engage together to removably attach the attachment body to the body.

The body may be u-shaped.

One embodiment is directed to a guide for directing a cutting instrument along a femur to remove an implanted femoral component with the femoral component including a proximal end that extends from the femur and includes a receptacle. The guide includes a first body with an upper section, a plurality of openings extending through the upper section, at least one sharpened flange extending outward from the upper section with the flanges positioned along the body radially outward from the openings, and a connector operatively connected to the upper body to engage with the receptacle in the component. The body also has an open end that includes a receiving section with opposing arms and a back section.

The connector may be positioned above the upper section.

Another embodiment is directed to a guide for directing a cutting instrument along a femur to remove an implanted femoral component with the femoral component including a proximal end that extends from the femur and includes a receptacle. The guide includes a body including opposing first and second sides, a plurality of openings extending through the second body, and a connector operatively connected to the body to engage with the receptacle in the component. The body includes an open interior section that is partially open. Further, the connector is positioned above tops of the plurality of openings.

Another embodiment is directed to a guide system for directing cutting instruments along a femur to remove an implanted femoral component with the femoral component including a proximal end that extends from the femur and includes a receptacle. The guide system includes a first body including: an upper section; a plurality of openings extending through the upper section; at least one sharpened flange extending outward from the upper section with the flanges positioned along the body radially outward from the openings; and a connector operatively connected to the upper body to engage with the receptacle in the component. The guide system also includes: a second body including opposing first and second sides; a plurality of openings extending through the second body; and a connector operatively connected to the body to engage with the receptacle in the component.

Another embodiment is directed to a method of cutting a femoral component from a femur, the femoral component includes a proximal end that extends from the femur and includes a receptacle. The method includes: positioning a first guide at a proximal end of the femur; applying a force to the guide and driving a sharpened flange on a bottom of the guide into the femur; engaging a first connector with the receptacle and attaching the first guide to the component; inserting a first osteotome into an opening in the first guide and cutting the femur with the first osteotome being inserted between the flange and the component; removing the first guide from the proximal end of the femur; positioning a second guide at the proximal end of the femur; engaging a second connector with the receptacle and attaching the second guide to the component; and inserting an osteotome into an opening in the second guide and cutting the femur.

The various aspects of the various embodiments may be used alone or in any combination, as is desired.

BRIEF DESCRIPTION OF THE DRAWINGS

FIG. 5 is a perspective view of a guide positioned at a proximal end of a femoral component.

FIG. 6 is a perspective view of a guide positioned at a proximal end of a femoral component with an osteotome extending through an opening in the guide.

DETAILED DESCRIPTION

Figure 1:
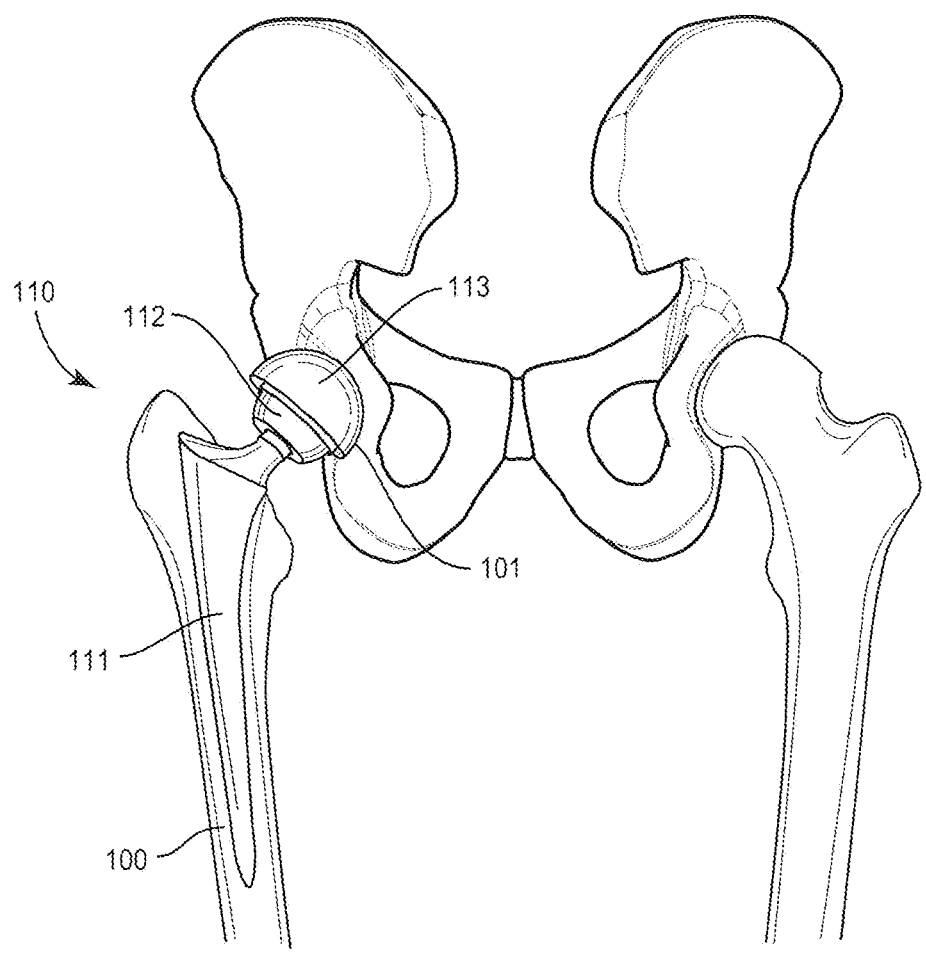
FIG. 1 is a side view of a hip implant with a femoral component mounted in a femur.
Figure 2:
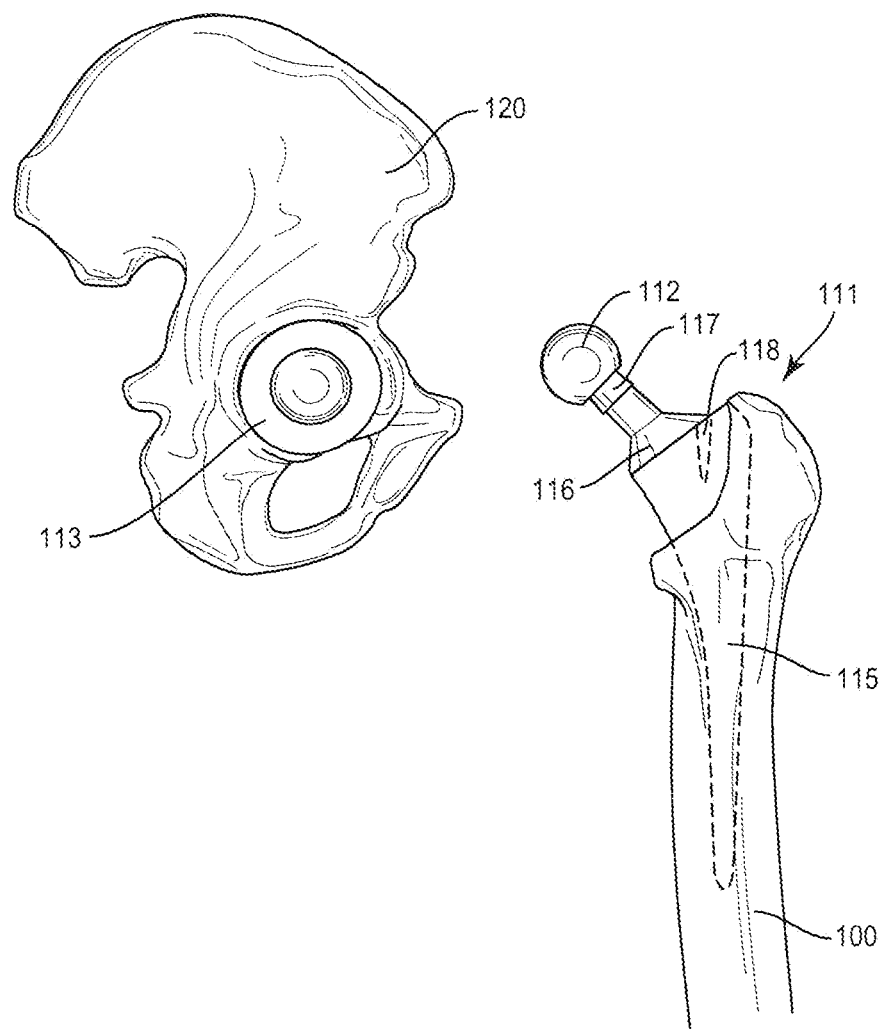
FIG. 2 is an exploded perspective view of a femoral component mounted in a femur and an acetabulum component mounted in a pelvis.

The present application is directed to one or more guides configured to attach to an implanted femoral component. The one or more guides are further configured to attach to a receptacle in the femoral component. The guides are shaped and sized to receive osteotomes for cutting the femoral component from the femur. The guides may also include one or more cutting edges that cut the femur around the femoral component.

In one embodiment, the device includes a pair of guides 20, 30 that are separately attached to the femoral component 111. A first guide 20 is mounted on the femoral component 111 to align and guide osteotomes 60 for cutting a first section of the femur 100. In one embodiment, the first section is a lateral section of the femur 100. The first guide 20 is removed and a second guide 30 is attached to the femoral component 111. The second guide 30 is configured to align and guide osteotomes for cutting a second section of the femur 100, such as a medial section. The cutting of the femur 100 using the first and second guides 20, 30 provides for removal of the component 111.

Figure 3:
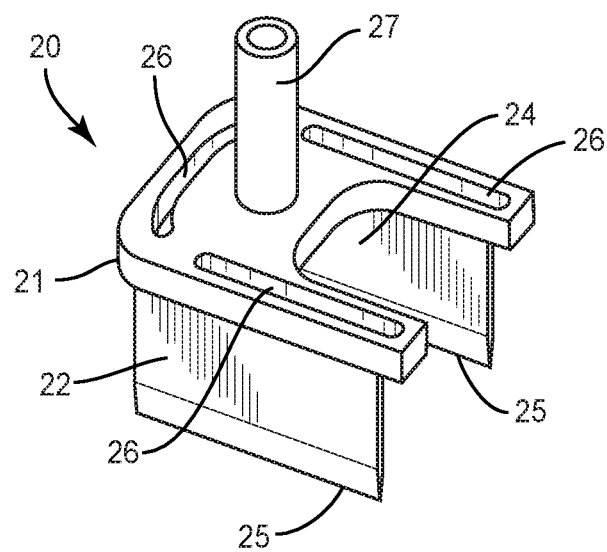
FIG. 3 is a perspective view of a guide.

FIG. 3 illustrates an embodiment of the first guide 20. In one embodiment, the first guide 20 is configured to attach to the lateral side of the femoral component 111. The guide 20 includes an upper body 21 with one or more outwardly-extending flanges 22. The guide 20 may include a single flange 22 that extends around a majority of the body 21, or two or more separate flanges 22. In one embodiment, the one or more flanges 22 extend outward from the body 21 in proximity to the outer edge of the body 21.

The guide 20 includes an indented receiving section 24 sized and shaped to extend around and receive the proximal section of the femoral component 111. This may include the neck 116, proximal stem 115, and/or mount 117 of the component 111. The receiving section 24 may be formed by a pair of opposing arms and a central section of the body 21. In one embodiment as illustrated in FIG. 3, the receiving section 24 includes a substantially U-shape. The receiving section 24 may be open along one side to facilitate placement of the guide 20 around the component 111.

The one or more flanges 22 include a sharpened edge 25 that cuts into the femur 100 during attachment of the guide 20 to the femoral component 111. The sharpened edge 25 may extend around an entirety or limited portion of the one or more flanges 22. In another embodiment, the ends of the one or more flanges 22 do not include sharpened edges.

One or more openings 26 are located on the body 21 with each configured to align and position an osteotome 60. The numbers of openings 26 may vary. In one embodiment, the openings 26 extend around the body 21 such that the osteotomes 60 can be inserted around different sections of the femoral component 111 for cutting and removal from the femur 100. The openings 26 may include a variety of different shapes and sizes. FIG. 3 includes the openings 26 extending through an interior of the body 21. Other embodiments may include exterior openings 26 formed by tracks that extend outward beyond the main portion of the body 21. In embodiments with multiple openings 26, each may include the same shape and configuration, or the different openings 26 may include different shapes and/or configurations.

Figure 4:
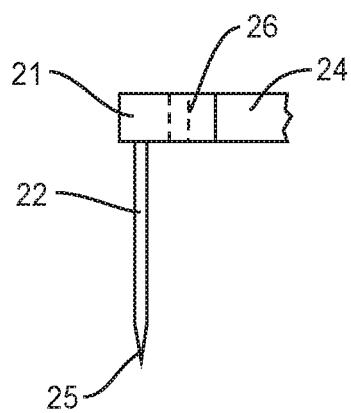
FIG. 4 is a partial side view of the guide of FIG. 3.

The openings 26 are positioned along the body 21 on the interior of the one or more flanges 22 as best illustrated in FIG. 4. This provides for the one or more flanges 22 to act as guides to direct the osteotomes 60 that are inserted through the openings 26. This positioning prevents the osteotomes 60 from moving too far away from the femoral component 111 during insertion.

The guide 20 also includes an attachment section 27 for attaching to the femoral component 111. The attachment section 27 is configured to align with and allow for attachment to the receptacle 118 that is located at the proximal end of the femoral component 111. The attachment section 27 is positioned to align with the receptacle 118 when the body 21 is positioned around the femoral component 111. In one embodiment as illustrated in FIG. 3, the section 27 includes an elongated tube. A connector (not illustrated) may be positioned within the section 27 to engage with the receptacle 118. In one embodiment, the connector is rotatably mounted to the tube and includes a body with threads, wings, or the like that attach to the receptacle 118.

In use, the guide 20 is moved over the femoral component 111. The flanges 22 are placed against the proximal end of the femur 100 in proximity to the component 111. The surgeon may then use an instrument to apply a striking forward to the top side of the body 21. This force causes the cutting edges of the flanges 22 to cut into the proximal end of the femur 100. This also positions the attachment section 27 at the receptacle 118. The attachment section 27 may be further aligned with the receptacle 118, and the connector is then inserted into the receptacle 118 and rotated to attach the guide 20 to the femoral component 111. The tube may further be hollow to receive a rotation tool for rotating the connector.

FIG. 5 illustrates an embodiment with the guide 20 attached to a proximal end of a femoral component 111. For clarity, the neck 116, mount 117, and head 112 of the femoral component 11 are not illustrated. Further, the femur 100 is not illustrated in FIG. 5 again for purposes of clarity. The guide 20 is sized to fit over and attach to the proximal end of the femoral component 111. In this embodiment, the guide 20 extends around the lateral side of the component 111. The body 21 is positioned over the proximal end, with the one or more flanges 22 extending along the sides. During insertion, the surgeon may apply a downward force to the body 21, such as with a striking instrument, to drive the flanges 22 into the femur 100. This action cuts the femur 100 to start the removal of the component 111. Once positioned, the attachment section 27 is aligned with the proximal end of the component 111. The connector in the tube may then be rotated to attach the guide 20 to the component 111.

Once the guide 20 is connected to the component 111, one or more osteotomes 60 are inserted through the openings 26 to further cut the femur 100. FIG. 6 illustrates an osteotome 60 inserted into one of the openings 26 and along the femoral component 111. The osteotome 60 extends behind the flanges 22 (i.e., between the flange 22 and the component 111). This provides for the flange 22 to direct the osteotome 60 along the component 111 and prevent movement away from the component 111 that could result in additional cutting of the femur 100.

The osteotome 60 includes one or more cutting edges 61 along a distal section. The distal tip 62 may be sharpened or otherwise configured to cut bone. The osteotomes 60 may include a variety of shapes and sizes. In the embodiment of FIG. 6, the osteotome 60 is substantially flat and includes a distal section 63 and a proximal section 64. The distal section 63 is inserted through the opening 26 and may include a shape that roughly matches the component 111. In the embodiment of FIG. 6, the distal section 63 includes a tapered width that roughly matches the taper of the component 111. The proximal section 64 may include a constant width which may facilitate positioning with the opening 26.

Osteotomes 60 of different shapes and sizes may be used in the different openings 26 along the guide 20. In one embodiment, the osteotome 60 includes a curved shape to match the curved opening along the lateral side of the guide 20.

Once the cutting of the femur 100 using the first guide 20 is complete, the guide 20 is removed from the component 111. This may include rotating the connector in an opposing direction to disconnect from the receptacle 118. Once disconnected, the guide 20 is removed from the component 111.

Figure 7:
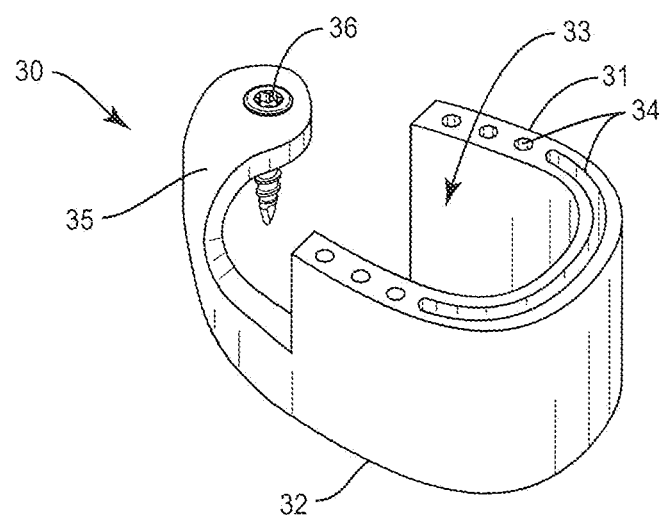
FIG. 7 is a perspective view of a guide.

A second guide 30 may then be attached to the component 111. FIG. 7 illustrates an embodiment of the second guide 30 which is configured to connect to the medial side of the component 111. The guide 30 is shaped and sized to fit around the neck 116, mount 117, and head 112 of the component 111 and seat against the femur 100.

The guide 30 includes a first side 31 and an opposing second side 32 that faces towards the femur 100 during use. The height of the guide 30 measured between the sides 31, 32 may vary. The guide 30 includes an interior space 33 sized to extend around the neck 116, mount 117, and head 112 of the component 111. The interior space 33 is not enclosed, but rather is open to provide for the guide 30 to be moved around the component 111.

One or more openings 34 extend through the guide 30. Each of the openings 34 is sized to receive an osteotome 60 as described above. The openings 34 may include a variety of sizes and shapes.

The guide 30 further includes an outwardly-extending arm 35 that extends over the component 111. The arm 35 includes a connector 36 rotatably attached and configured to engage with the receptacle 118 in the component 111. The connector 36 may include an enlarged head that is exposed on the first side 31 and an elongated body with threads or other mechanical aspects to attach with the receptacle 118.

Figure 8:
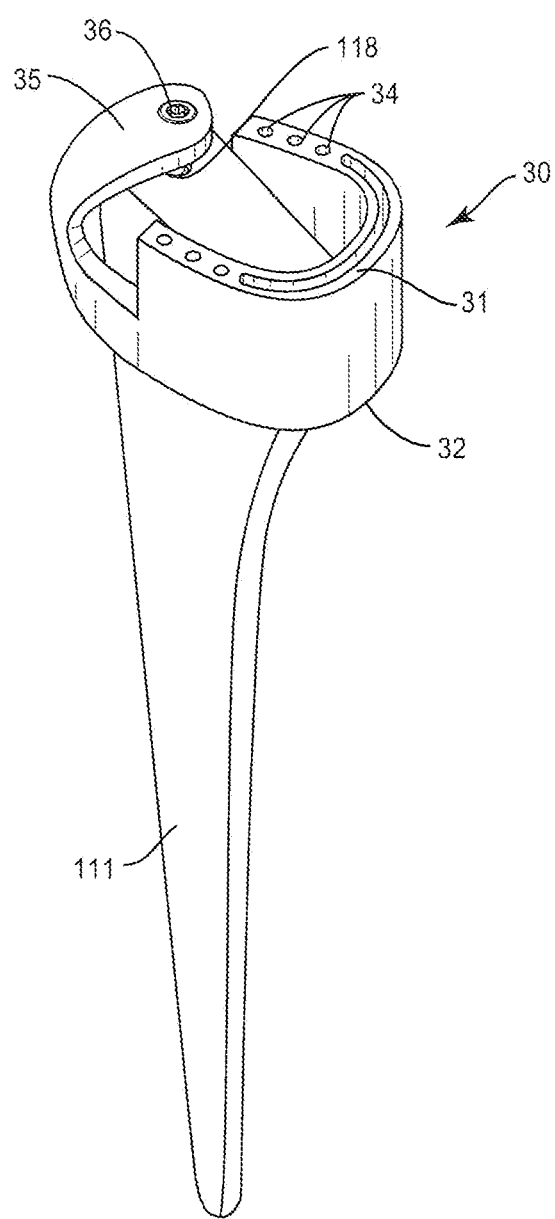
FIG. 8 is a perspective view of a guide positioned at a proximal end of a femoral component.

In use, the guide 30 is positioned at the proximal end of the component 111 as illustrated in FIG. 8. The second side 32 is positioned against the femur 100 with the interior space 33 receiving the component 111. The arm 35 is positioned over the proximal end of the component 111 such that the connector 36 can extend into and engage with the receptacle 118. Once attached, one or more osteotomes 60 are inserted through the openings 34 to cut the femur 100. Once the cutting is complete, the connector 36 is detached from the receptacle 118, and the guide 30 is removed from the component 111.

Figure 9:
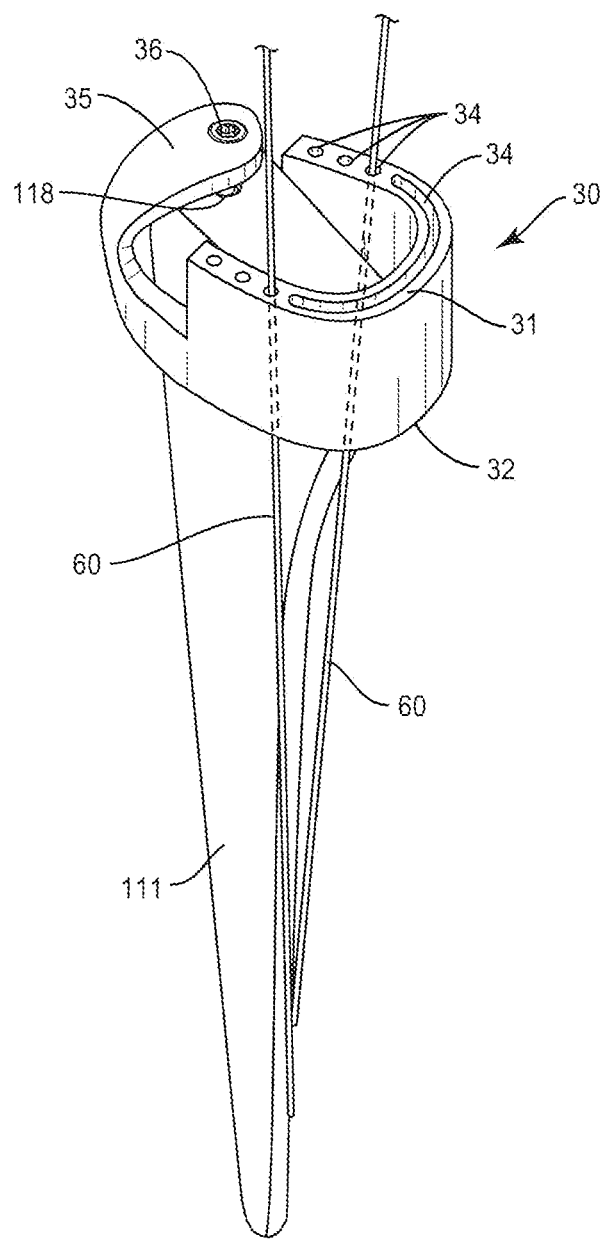
FIG. 9 is a perspective view of a guide positioned at a proximal end of a femoral component with osteotomes extending through openings in the guide.

FIG. 9 illustrates osteotomes 60 inserted into a pair of the openings 34 in the guide 30. These osteotomes 60 are shaped as elongated pins that fit through the openings 34 and along the femoral component 111. The osteotomes 60 include a sharpened distal end and/or sharpened edges that cut the bone around the femoral component 111. The openings 34 may extend substantially perpendicular to the top of the guide 30, or they may be positioned at various angles to facilitate insertion and cutting of the bone.

Figure 10:
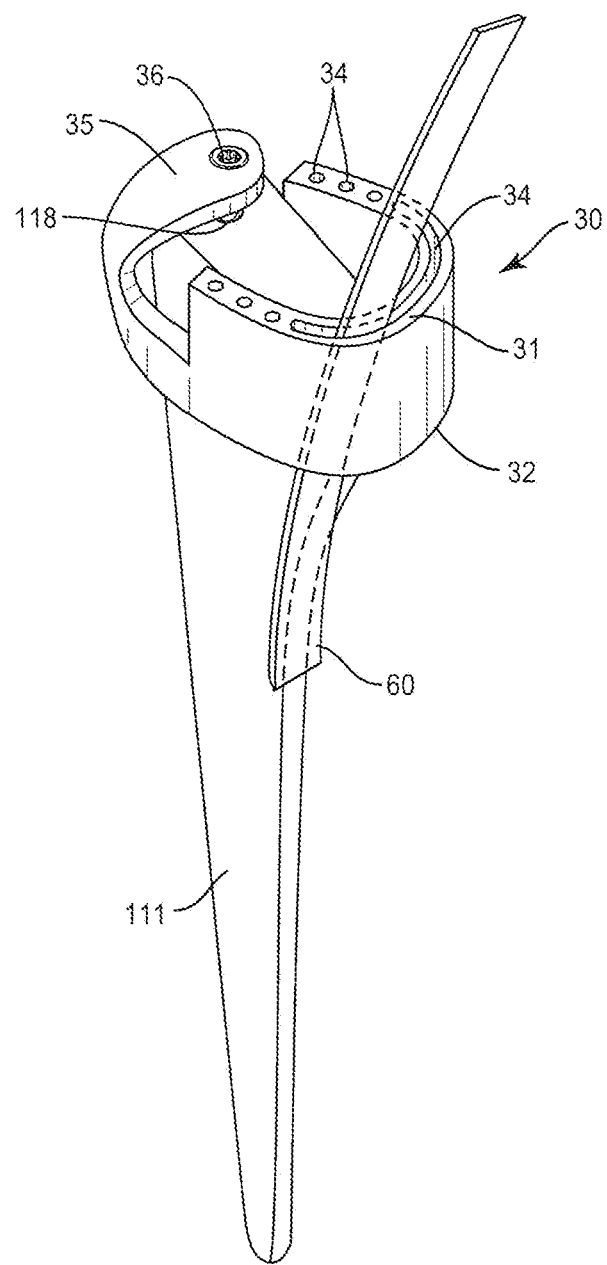
FIG. 10 is a perspective view of a guide positioned at a proximal end of a femoral component with an osteotome extending through an opening in the guide.

FIG. 10 illustrates another osteotome 60 inserted into the elongated opening 34 at the medial end of the guide 30. The position of the opening 34 and construction of the osteotome 60 provides for cutting the bone along the curved neck and stem on the medial side of the femoral component 111. The osteotome 60 may include a curved shape, or may be flexible to conform to the curvature of the opening 34. The width of the osteotome 60 may vary, with FIG. 10 including the osteotome 60 having a width that extends along less than ½ of the length of the opening 34. The curvature of the opening 34 may be consistent along the length to allow the osteotome 60 to be slid and/or inserted at different areas along the length to facilitate cutting the bone.

The system may be used with the first guide 20 initially used to cut a lateral section of the femur 100, followed by the second guide 30 being attached to cut a medial section of the femur 100. The process may also be reversed with the second guide 30 initially used to cut a first section of the femur 100, followed by the first guide 20 being attached to cut a second section of the femur 100. In these embodiments, just one of the guides 20, 30 is positioned at the component 111 at one time.

In another embodiment, both guides 20, 30 are positioned at the component 111 at the same time.

The embodiments described above include a structure to mechanically attach each of the guides 20, 30 to the component 111. Other embodiments may not include a mechanical attachment. These embodiments may include the one or more guides 20, 30 sized to be placed at the component 111. The guides 20, 30 are not attached to the component 111 during the use of the osteotomes.

In one embodiment, the first and second guides 20, 30 may each include a substantially similar attachment mechanism and fastener. By way of example, each guide 20, 30 may include an attachment section 27. Another example includes each guide 20, 30 including an arm 35. The attachment section 27 and arm 35 may each include a connector that engages with the receptacle 118.

The side 32 of the second guide 30 may include one or more cutting edges that are driven into the femur 100 by applying a force to the guide 30.

Figure 11:
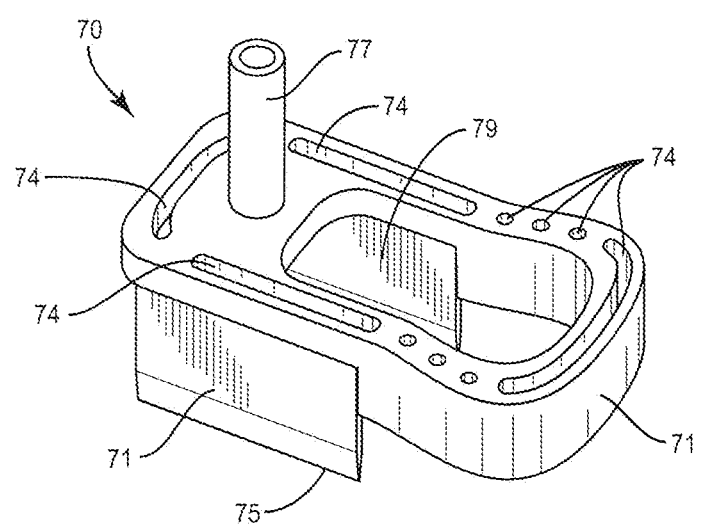
FIG. 11 is a perspective view of a guide.

The device may include a single piece that extends overall lateral and medial sections of the femoral component 111. FIG. 11 illustrates an embodiment with the guide 70 including a single body 71. In this embodiment, the body extends completely around and forms an enclosed interior 79. Other embodiments may include one or more openings in the body 71 leading into the interior 79. The body 71 includes a variety of openings 74 to receive and guide osteotomes for cutting the bone. A single attachment section 77 is positioned along the upper section of the body 71. The attachment section 77 may include a connector (not illustrated) or various other mechanical features to attach to the receptacle 118 in the femoral component 111.

In the embodiment of FIG. 11, the portion of the body 71 that is aligned over the lateral section of the component 111 includes a greater height (measured between upper and lower edges) that a medial section. The lateral section includes one or more sharpened edges 75 that may be used to cut the bone upon application of a force to the guide 70. The medial section includes a smaller height and may include a non-sharped lower end.

The guide 70 of FIG. 11 is constructed as a single piece. Another embodiment may include the guide constructed as two or more separate pieces that may be attached together. The separate pieces may include tracks that engage together when the pieces are both positioned on the femoral component 111. Other attachment mechanisms may also be used to attach the separate pieces, including but not limited to mechanical fasteners, ball-and-detent arrangement, snap fit engagements. In these various embodiments, a first piece may be positioned on the femoral component 111. Thereafter, a second piece is moved into position on the femoral component and attached to the first piece. Additional pieces may be added. Once the cutting of the bone is complete, the various pieces may be detached in a similar manner. Alternatively, the pieces may remain attached and be removed in combination with the component 111.

Figure 12:
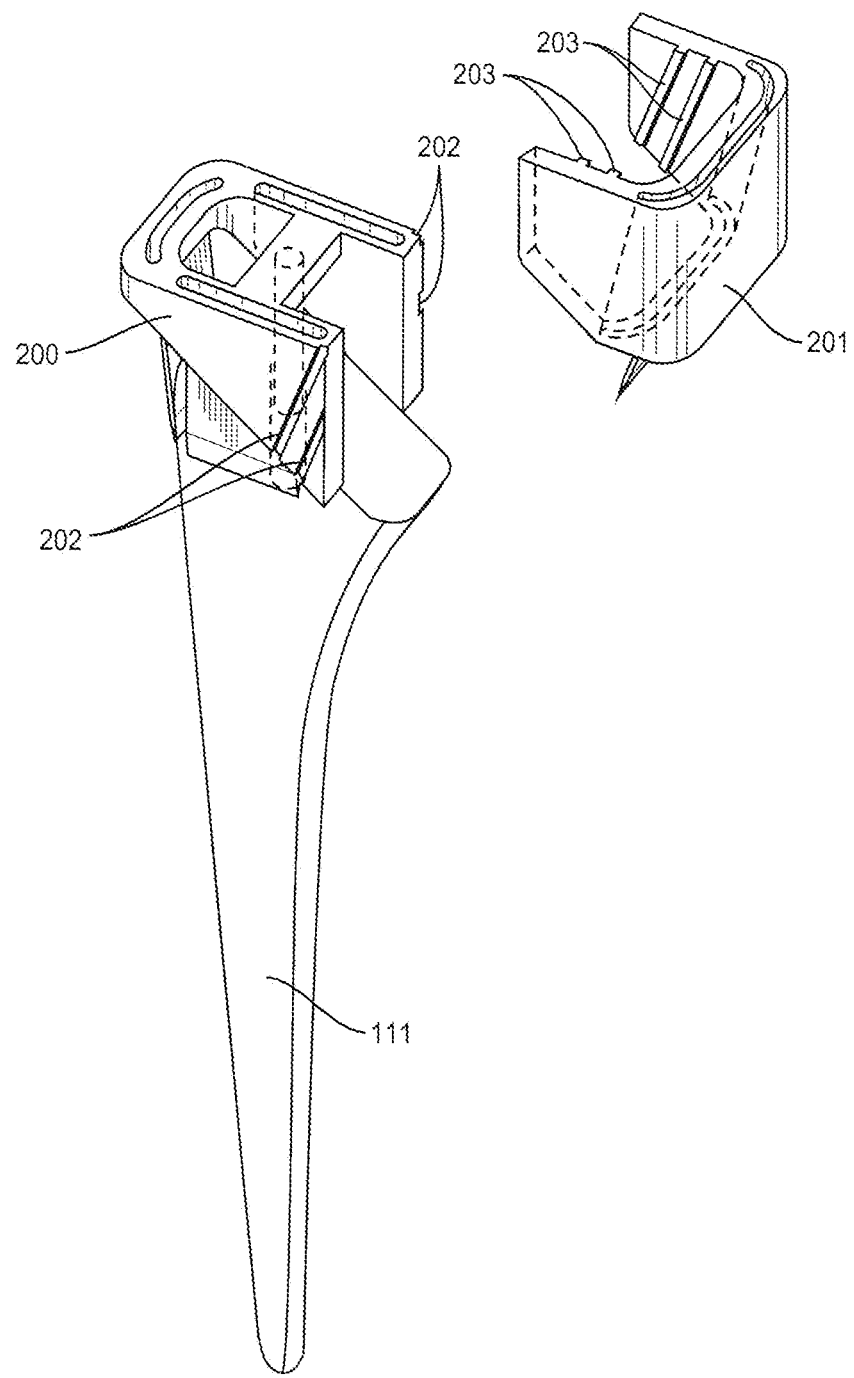
FIG. 12 is a perspective view of first and second guides separated apart.

FIG. 12 illustrates an embodiment with a first guide 200 configured to be positioned on a first portion of the component 111, and a second guide 201 configured to be positioned on a second portion. The guides 200, 201 each include rails 202, 203 configured to engage together. In this embodiment, rails 202 extending into the guide 200 (i.e., female rails) and rails 203 extend outward from the guide 201 (i.e., male rails). The rails 202, 203 are sized to engage together. The rails 202, 203 may be positioned at a non-perpendicular angle relative to a top surface. The angle may conform to the approach angle used for positioning the guides 200, 201 on the component 111. The angle may further prevent inadvertent detachment of the guides 200, 201 once they become attached together.

Figure 13:
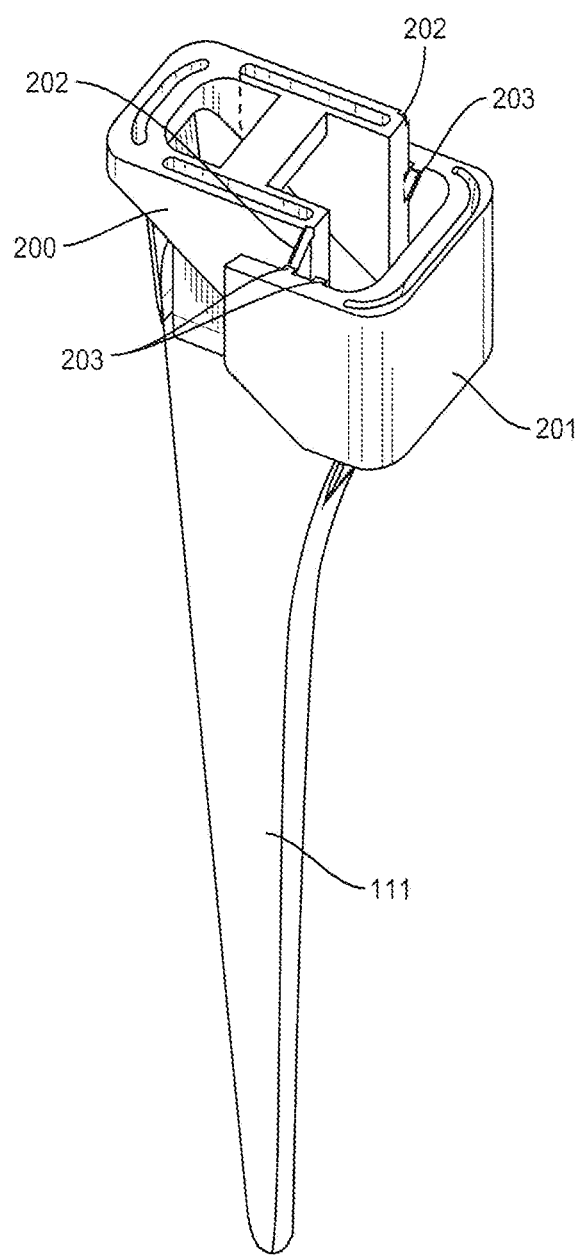
FIG. 13 is a perspective view of first and second guides in the process of being positioned together on the femoral component.

FIG. 13 illustrates the two guides 200, 201 being attached together with the rails 202, 203 engaging together.

Figure 14A:
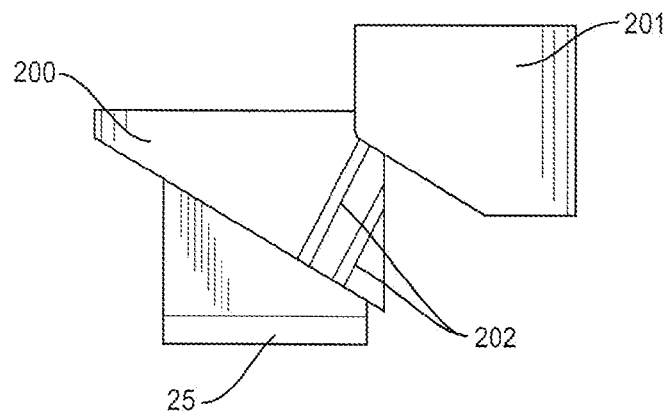
FIGS. 14A-14C illustrate side views of relative positions of first and second guides.
Figure 14B:
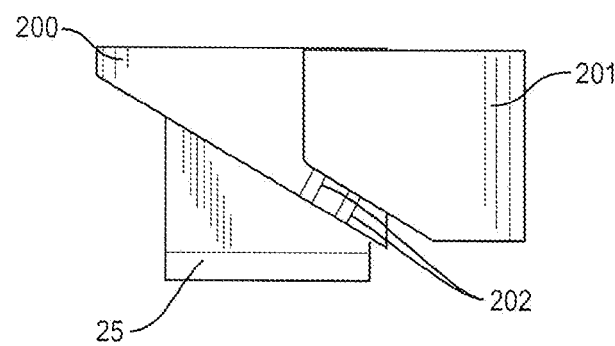
Figure 14C:
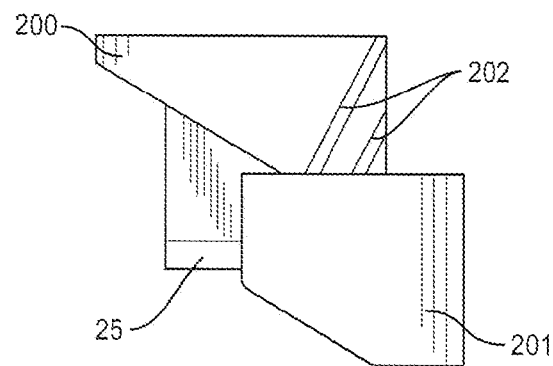

FIGS. 14A-14C illustrate side views of the guides 200, 201 being attached together. The relative positions of the guides 200, 201 may vary, and may include the second guide 201 positioned above the first guide 200 as illustrated in FIG. 14A, the upper sides of the guides 200, 201 positioned at the same level as illustrated in FIG. 14B, and the second guide 201 positioned below the first guide 200 as illustrated in FIG. 14C.

The guides 200, 201 may attach together solely through engagement with the rails 202, 203. Additional mechanisms may also be used, including a ball and detent arrangement along the rails, and a mechanical fastener that contacts each guide 200, 201.

The openings that extend through the guides may be positioned at various angles through the guide bodies. This may include the angles varying axially and/or radially along the length. FIG. 10 includes an embodiment in which the enlarged opening 34 may be angled inward to facilitate positioning of the osteotome 60 in proximity to the curved medial border of the component 111. The bodies of the guides may have variable heights and/or widths and/or lengths to accommodate the various angles of the openings to position the osteotomes.

The relationship between the osteotome and the implant can be either perfectly matched in regard to size, angle, curve (requiring a different guide for each implant size and design) or less exact to allow for extraction of multiple sizes and designs. Ideally a very size and design specific system would be created to minimize the amount of bone destruction required to remove, and ensure that all interfaces are adequately disrupted for extraction.

The various guides 30 may be configured to receive and position specific osteotomes. By way of example, a first guide 30 may be configured to attach to the medial side of the femoral component 111. The first guide 30 is configured to receive and position a curved osteotome along the curved medial surface of the stem 115. A second guide 30 may be configured to be attached to the lateral side of the femoral component. The second guide 30 is configured to receive and position a substantially straight osteotome that matches the straight lateral edge of the femoral component 111. The various guides 30 provide for accommodate specific osteotomes 60 that will be cutting along specific sections of the femoral component 111.

Osteotomes are one type of cutting tool that may be used with the device 10. Various other types of cutting tools may also be used with each being configured to be directed by the various guides 26 to be moved beyond the body 20 and cut the femur 100. The cutting tools include one or more cutting edges. The cutting tools 100 may include different shapes, sizes, and constructions.

The embodiments described above are directed to a guide for engaging with a femoral component of a hip replacement implant. The guide may also be used for other surgical applications for use in engaging with an implanted device for guiding one or more osteotomes. The guides for these applications may have a variety of different shapes and sizes that conform to the implanted devices.

The various implants and insertion tools may be used during surgical procedures on living patients. These may also be used in a non-living situation, such as within a cadaver, model, and the like. The non-living situation may be for one or more of testing, training, and demonstration purposes.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. The present embodiments are, therefore, to be considered in all respects as illustrative and not restrictive.

What is claimed is:

1. A guide configured to direct one or more osteotomes to remove a femoral component that is implanted in a femur, the femoral component including a stem implanted within the femur, a proximal end that extends from the femur, and a receptacle in the proximal end, the guide comprising:
- a body with a closed end and opposing sides that are spaced apart and extend from the closed end, the body including an open end formed between the sides and opposite from the closed end, the body forming an interior space between the sides and the closed end with the open end leading into the interior space, the body sized to extend partially around a perimeter of the femoral component when the femoral component is positioned in the interior space;
- the body including a thickness measured between an inner side wall that faces into the interior space and an opposing outer side wall;
- an extension that extends outward from one of the closed end and the sides and over the interior space, the extension sized to extend over the proximal end of the femoral component; and
- a connector positioned in and extending from the extension to mount in the receptacle to attach the guide to the femoral component.

2. The guide of claim 1, further comprising a flange that extends outward from a bottom side of the body and comprising a sharpened tip to cut into the femur.

3. The guide of claim 2, wherein the flange extends outward from each of the closed end and the opposing sides.

4. The guide of claim 2, further comprising a slot that is enclosed within and that extends through the body, the slot including an inlet at a top side of the body and an outlet at the bottom side of the body, the slot extending through the body between the flange and the inner side wall.

5. The guide of claim 4, further comprising openings that extend through the body from the top side to the bottom side, the openings being smaller than the slot and also extending through the body between the flange and the inner side wall.

6. The guide of claim 2, wherein the flange comprises a smaller thickness than the body.

7. The guide of claim 1, further comprising an attachment body configured to removably attach to the sides of the body and extend across the open end to fully enclose the interior space, each of the attachment body and the sides including attachment mechanisms that engage together to removably attach the attachment body to the sides.

8. The guide of claim 1, further comprising a tube that is attached to and extends from the extension, the tube including an opening sized to receive the connector.

9. A guide configured to guide one or more osteotomes to remove a femoral component that is implanted in a femur, the femoral component including a stem implanted within the femur, a proximal end that extends from the femur, and a receptacle in the proximal end, the guide comprising:
- a U-shaped body with a closed end and opposing sides with inner side walls that form an interior space with an open end sized to receive the femoral component, the body comprising a top side that faces away from the femur when positioned on the femoral component and an opposing bottom side;
- one or more elongated slots that are enclosed within and that extend through the body from the top side to the bottom side and are sized to receive the osteotomes, each of the one or more slots comprising an inlet at the top side and an outlet at the bottom side of the body; and
- a flange that extends from the bottom side of the body and comprises a sharpened tip to cut into the femur, the flange extending from the bottom side of the body between the one or more elongated slots and outer side walls of the body.

10. The guide of claim 9, wherein the flange is divided into two or more separate sections that each extend around different sections of the body.

11. The guide of claim 9, wherein the flange comprises a thickness measured between an inner side and an outer side, the thickness of the flange being smaller than that of the body.

12. The guide of claim 9, further comprising an attachment body removably attached to the body to enclose the interior space, each of the body and the attachment body including attachment members that engage together to removably attach the attachment body to the body.

13. The guide of claim 9, further comprising an extension that extends from the top side of the body over the interior space and over the receptacle in the femoral component when the body is positioned around the femoral component, the extension being spaced away from the open end.

14. The guide of claim 13, further comprising a connector that extends outward from the extension to engage with the receptacle in the femoral component to attach the guide to the femoral component.

15. A guide configured to guide one or more osteotomes to remove a femoral component that is implanted in a femur, the femoral component including a stem implanted within the femur, a proximal end that extends from the femur, and a receptacle in the proximal end, the guide comprising:
- a body with a closed end and opposing sides that are spaced apart and extend from the closed end, the body including an open end formed between the sides and opposite from the closed end, the body forming an interior space between the sides and the closed end with the open end leading into the interior space, the body sized to extend partially around a perimeter of the femoral component when the femoral component is positioned in the interior space;
- the body comprising a top side that faces away from the femur when positioned on the femoral component and an opposing bottom side;
- an extension that extends outward from the top side of the body and over the interior space, the extension sized to extend over the proximal end of the femoral component when the femoral component is positioned in the interior space; and
- a connector positioned in and extending from the extension to mount in the receptacle to attach the guide to the femoral component;
- one or more elongated slots that extend through the body from the top side to the bottom side and that are sized to receive the osteotomes, each of the one or more slots comprising an inlet at the top side and an outlet at the bottom side of the body; and
- a flange that extends from the bottom side of the body and comprise a sharpened tip to cut into the femur, the flange extending from the bottom side of the body between the one or more elongated slots and inner side walls of the body.

16. The guide of claim 15, further comprising a tube that extends from the extension and is sized to receive the connector.

17. The guide of claim 15, wherein the flange is divided into two or more separate sections that each extend around different sections of the body.

18. The guide of claim 15, wherein the flange comprises a thickness measured between an inner side and an outer side, the thickness of the flange being smaller than that of the body.

19. The guide of claim 15, further comprising an attachment body removably attached to the body to enclose the interior space, each of the body and the attachment body including attachment members that engage together to removably attach the attachment body to the body.

20. The guide of claim 15, wherein the body is u-shaped.

* * * * *